(12) United States Patent
Koneru

(10) Patent No.: US 7,885,824 B1
(45) Date of Patent: *Feb. 8, 2011

(54) METHOD AND SYSTEM FOR DELIVERING MEDICAL THERAPIES

(75) Inventor: Phanesh Koneru, Ashburn, VA (US)

(73) Assignee: Exela Pharmsci, Inc., Ashburn, VA (US)

( * ) Notice: Subject to any disclaimer, the term of this patent is extended or adjusted under 35 U.S.C. 154(b) by 1160 days.

This patent is subject to a terminal disclaimer.

(21) Appl. No.: 11/478,240

(22) Filed: Jun. 29, 2006

Related U.S. Application Data

(63) Continuation-in-part of application No. 11/444,670, filed on Jun. 1, 2006, now abandoned, which is a continuation-in-part of application No. 11/298,196, filed on Dec. 9, 2005, now abandoned.

(60) Provisional application No. 60/634,898, filed on Dec. 10, 2004.

(51) Int. Cl.
G06Q 10/00 (2006.01)
G06Q 50/00 (2006.01)

(52) U.S. Cl. ......................................................... 705/2

(58) Field of Classification Search ...................... 705/2, 705/4; 600/300
See application file for complete search history.

(56) References Cited

U.S. PATENT DOCUMENTS

| 5,619,991 | A | 4/1997 | Sloane |
| 5,845,255 | A | 12/1998 | Mayaud |
| 6,014,631 | A | 1/2000 | Teagarden et al. |
| 6,045,501 | A | 4/2000 | Elsayed et al. |
| 6,063,026 | A | 5/2000 | Schauss et al. |
| 6,315,720 | B1 * | 11/2001 | Williams et al. ............ 600/300 |
| 6,561,976 | B2 | 5/2003 | Elsayed et al. |

(Continued)

OTHER PUBLICATIONS

Isotretinoin Risk Management Information (iPLEDGE and SMART).

(Continued)

Primary Examiner—Gerald J. O'Connor
Assistant Examiner—John A Pauls
(74) Attorney, Agent, or Firm—Frommer Lawrence & Haug LLP; Brian J. Martin

(57) ABSTRACT

A method for delivering a to a patient a medical therapy, which was previously characterized as a high-risk medical therapy, with restricted distribution or access under one or more restricted access programs, including programs with little or no restricted access. The medical therapy previously required a restricted distribution program that included registration of the physician, patient, or distributor in a computer readable medium prior to distribution. The method involves providing to a distributor or third party reviewer prescription data authorizing distribution of the medical therapy to a specific patient in need of the medical therapy and confirming the patient is eligible to receive the medical therapy and understands the risks associated with the medical therapy by the distributor or third party reviewer. The distributor or third party reviewer determines the qualified patient's eligibility for access to the medical therapy determines if the patient is eligible independent of requiring a registration of either the physician, patient, or distributor, in a computer readable medium, or a validation code. Over time, the patient's risk level may be reassessed by the patient's physician, a distributor, or a third party reviewer. In addition, the medical therapy itself may be re-characterized to a lower or higher risk level, requiring the adjustment of the previously required controls placed on the product.

24 Claims, 4 Drawing Sheets

U.S. PATENT DOCUMENTS

| | | |
|---|---|---|
| 6,561,977 B2 | 5/2003 | Williams et al. |
| 6,755,784 B2 | 6/2004 | Williams et al. |
| 6,869,399 B2 | 3/2005 | Williams et al. |
| 6,908,432 B2 | 6/2005 | Williams et al. |
| 2004/0117126 A1 | 6/2004 | Fetterman |
| 2004/0117205 A1 | 6/2004 | Reardan et al. |
| 2004/0122713 A1 | 6/2004 | Hill et al. |
| 2004/0152960 A1 | 8/2004 | Elsayed et al. |
| 2005/0106544 A1 | 5/2005 | Joshi et al. |
| 2005/0108053 A1 | 5/2005 | Jones, Jr. |
| 2005/0176768 A1 | 8/2005 | Williams et al. |
| 2005/0215869 A1 | 9/2005 | Elsayed et al. |
| 2005/0222874 A1 | 10/2005 | Reardan et al. |
| 2005/0240442 A1 | 10/2005 | Lapsker |

OTHER PUBLICATIONS

Thalomid® Risk Management Information (S.T.E.P.S.).
Clozaril® Risk Management Information (Clozaril National Registry (CNR)).
Xyrem® Risk Management Information (Physician Success Program).
Revlimid® Risk Management Information (Rev Asst).
Tracleer® Risk Mangement Information (Tracleer Access Program (T.A.P.)).

* cited by examiner

US 7,885,824 B1

METHOD AND SYSTEM FOR DELIVERING MEDICAL THERAPIES

CONTINUATION DATA

This application is a continuation-in-part of U.S. application Ser. No. 11/444,670 filed Jun. 1, 2006, now abandoned which is a continuation-in-part of U.S. application Ser. No. 11/298,196, filed Dec. 9, 2005, now abandoned and claims the benefit of U.S. provisional application 60/634,898, filed Dec. 10, 2004.

FIELD OF INVENTION

The present invention relates generally to a system and method for delivering medical therapies to a patient. More particularly, the present invention relates to a system and method for delivering a medical therapy, which was previously characterized as a high-risk medical therapy and required a restricted distribution program, to a patient while preventing access to the medical therapy for individuals for whom the medical therapy would be contraindicated or otherwise restricted.

BACKGROUND DISCUSSION

Conventional medical therapies are typically associated with certain risks and benefits for patients. In many instances, these risks and benefits may be managed by effective counseling between a prescribing physician and patient, based on information provided by the product's labeling and other available information.

Medical therapies that pose risks that require additional patient compliance or monitoring, however, may not be as effectively managed by the prescribing physician and patient. Indeed, in some instances, these medical therapies may only be distributed, or the patient provided access to these medical therapies, according to additional requirements described in the product's labeling or as a condition for product marketing. In addition, a patient's risk level may change over time, requiring a reassessment of the appropriate risk management program, including programs with little or no restrictions. Conventional distribution methods typically rely on the prescribing physician or dispensing pharmacist to read and follow these labeling requirements. In some instances, a regulatory authority, such as, the U.S. Food and Drug Administration (FDA), has required the development of a restricted distribution or access program prior to market approval for the medical therapy. Conventional restricted distribution or access programs typically required that physicians, patients, pharmacies, or wholesalers be pre-registered prior to prescribing or dispensing medical therapies. Other conventional distribution programs required that patients be assigned to certain risk categories before generating prescription validation codes in a computer readable medium, or that prescriptions be dispensed only after verifying the prescription validation codes in a computer readable medium. In some instances, these validation codes were generated following the assignment of patients to certain risk groups and certain requirements being met by a patient assigned to the group, including diagnostic testing.

In yet other instances, patient data may be entered into a computer database before distributing the medical therapy with steps requiring a confirmation that the prescriber has the ability to prescribe and certain patient educational materials have been read and generation of periodic reports regarding the distribution of the medical therapy via the computer database.

One example of a conventional restricted access program is the program approved as part of the labeling for Clozaril® (clozapine) that requires pharmacies to be pre-registered to dispense the drug only to patients for whom baseline and periodic white blood cell counts have been taken. This system requires the pharmacist to monitor compliance with the requirements of the restricted drug access program approved as part of the approved labeling for the drug product.

Another example of a conventional restricted access program is the System for Thalidomide Education and Prescribing Safety (S.T.E.P.S.®), which was approved as part of the labeling for Thalomid® (thalidomide) and requires, among other things, that physicians, patients, and pharmacies be pre-registered in a computer readable medium and the generation of a prescription code following the necessary registrations and an interactive voice response system survey. This code must be entered on the registered patient's prescription by a registered prescriber and later verified by a registered pharmacist prior to dispensing the drug. Another example is the restricted distribution program, Tracleer Access Program (T.A.P.), which was approved as part of the labeling for Tracleer® (bosentan).

One example of a system for delivering medical therapy is described in U.S. Pat. No. 6,561,976, issued to Elsayed et al., entitled, "Methods for Delivering a Drug to a Patient While Preventing the Exposure of a Fetus or Other Contraindicated Individual to the Drug." This relates to a method for delivering a teratogenic drug a patient while preventing fetal exposure to the drug. This method involves registering, in a computer readable storage medium, physicians permitted to prescribe the drug, and registering the patient, in a computer readable medium, including the patient's ability to become pregnant or impregnate a female. Following these and other steps, the patient is provided access to the drug only after "verifying" that the patient is either incapable of becoming pregnant or is not currently pregnant by consulting one or more databases.

Another example is provided in U.S. Pat. No. 6,869,399, issued to Williams et al., entitled, "Methods for Delivering a Drug to a Patient While Restricting Access to the Drug By Patients for Whom the Drug May be Contraindicated." This relates to a method for permitting prescriptions to the teratogenic drug thalidomide only after a pharmacy has become aware of approval of a prescription for thalidomide for the patient from a computer readable storage medium. The prescription approval in the computer readable storage medium is generated after assigning the patient to a risk group and then determining that the risk from administering the drug is acceptable.

Yet another example is provided in U.S. Patent Pub. No. US 2005/0215869, by Elsayed et al. entitled "Methods for Delivering a Drug to a Patient While Preventing the Exposure of a Foetus or Other Contraindicated Individual to the Drug." This relates to a method for delivering a drug to a patient while preventing the exposure of a fetus or other contraindicated individuals to the drug. This method involves receiving information from a prescriber including information about the prescriber, patient, and medical therapy and entering the data in a computer database prior to distributing the drug. Prior to distributing the drug, a confirmation is made that a prescriber has the ability to prescribe the drug and patient educational materials have been read. Periodic reports are generated regarding the distribution of the drug via the computer database.

SUMMARY OF THE INVENTION

The present invention is directed toward a method and apparatus for delivering a medical therapy that was previously characterized as a high risk medical therapy, while preventing access to the medical therapies for individuals for whom the medical therapy would be contraindicated or otherwise restricted. The medical therapy previously required a restricted distribution program that included registration of the physician, patient, or distributor in a computer readable medium prior to distribution The distributor determines patient access to the drug following a physician prescription and initial risk level assessment by the patient's physician.

Accordingly, one embodiment of the present invention relates to a method and apparatus for determining whether a patient meets requirements for access to the medical therapy. The method involves receiving prescription data from a physician authorizing distribution of the medical therapy to a specific patient in need of the medical therapy, and confirming that the patient is eligible to receive the medical therapy and that the patient understands the risks associated with the medical therapy. The medical therapy is distributed independent of registration of the physician, patient, or distributor, or a combination thereof, in a computer readable medium prior to the distribution of the medical therapy, or a validation code.

Another embodiment of the present invention relates to the embodiment described above, and, further, providing a data collection method for obtaining patient, physician, or distributor data.

Yet another embodiment of the present invention relates to the embodiment described above, and, further, an article of manufacture to be distributed in interstate commerce according to the method for delivering the medical therapy, wherein the article comprises a pharmaceutical dosage form comprising a drug substance for administration to the patient and labeling to be accompanied with the dosage form.

Yet another embodiment of the present invention relates to the embodiment described above and, further, limiting the distribution of the medical therapy to certain patient populations.

Yet another embodiment of the present invention relates to the embodiment described above and, further, limiting the distribution of the medical therapy for the treatment of certain indications.

DETAILED DESCRIPTION OF THE INVENTION

Figure 1:
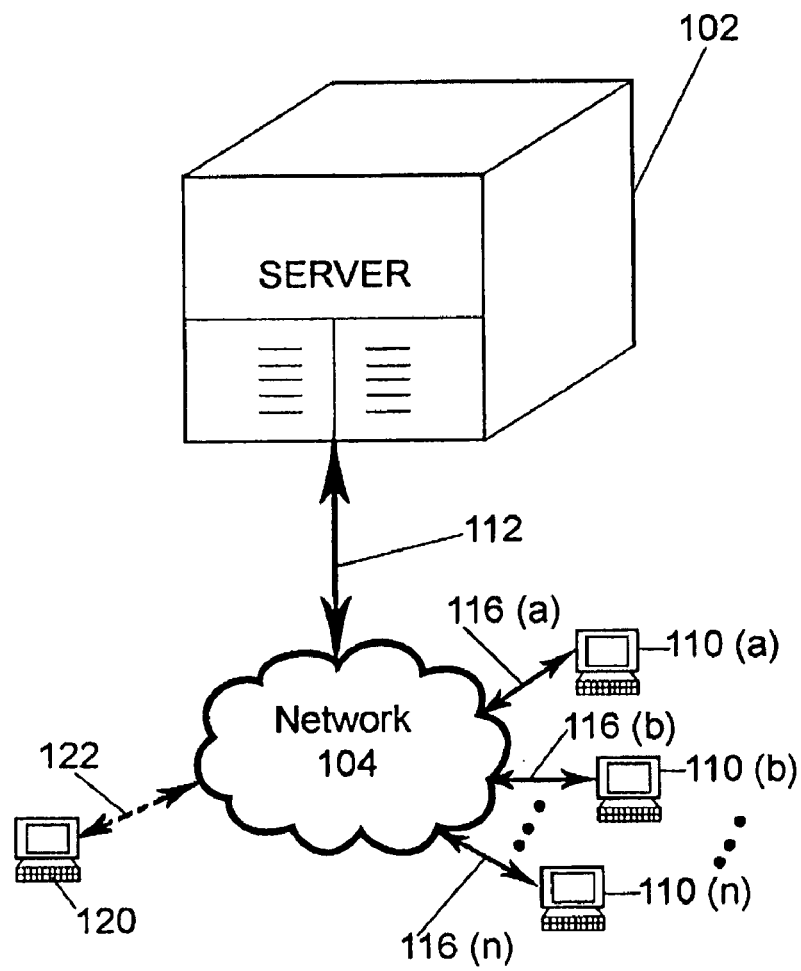
FIG. 1 shows a network environment adapted to support the present invention.

Generally, the present invention relates to a system and method for delivering medical therapies to a patient. More particularly, this invention relates to a system for: 1) determining a patient's access to the medical therapy after it has been prescribed and 2) a method for delivering the medical therapy to the patient or permitting the patient to obtain access to the medical therapy under one or more restricted access programs, including programs with little or no restricted access. In many cases, the medical therapy was previously characterized as a high-risk therapy and required a restricted distribution program, to a patient. The invention also provides a system and method to adjust the patient's risk level over time to determine the appropriate access to the medical therapy.

While it has been possible to apply this invention to a variety of medical therapies, one embodiment of the present invention may be used to deliver a drug with the potential for serious adverse events to the patient or a developing fetus or with the potential for substance abuse.

The present invention provides a solution for delivering a restricted access or distribution medical therapy that may not be effectively managed by the prescribing physician and patient alone, or, optionally, with the involvement of the dispensing pharmacist. Because of the unique and sometimes complex restricted distribution systems associated with a particular medical therapy, conventional techniques have not provided a method that permits access to the medical therapy while providing additional support for the physician's decision to prescribe the medical therapy. The medical therapy may be provided by one other than the prescriber. In some aspects, the present invention, provides the support without requiring pre-registration steps for either the physician, or the patient, or the pharmacy. The assignment of patients to certain risk categories may not be necessary. Generating validation codes or verifying validation codes in a computer readable medium may not be needed.

An embodiment of the invention is a restricted distribution system for a generic version of the reference listed drug Thalomid® (thalidomide). While the present invention provides a restricted distribution delivery means for the teratogenic drug thalidomide, the invention also may be employed for distributing any high risk medical therapy that involves a restricted distribution or access program, such as the drugs referred to herein, for example, clozapine, thalidomide, lenalidomide, isotretinoin, bosentan, alosetron, dofetilide, or drugs with a high abuse potential, which may be regulated in part by the U.S. Drug Enforcement Agency (DEA), such as oxycodone, marijuana, and cannabis.

A "high risk medical therapy" as used herein may refer to a medical therapy that poses an unacceptable risk or serious adverse event that should be avoided in certain patients, while in certain other patients the medical therapy may be used relatively safely if the drug manufacturer's labeling instructions are followed closely. The phrase "adverse event" may refer to an undesirable event but is incidental to the use of a drug in a given patient. An adverse event may include a simple event such as transient headache or rash or a serious event such as toxicity or failure of vital organs such as liver, kidney, heart, brain or lungs, teratogenicity, or even death.

According to the present invention, prior to the distributor receiving a prescription, a physician may determine that a particular therapy is beneficial to a patient first by identifying the requirements necessary for the patient to obtain access to the medical therapy. The physician may then explain to the patient the medical therapy, its risks and benefits, and the requirements for access to the medical therapy.

If the physician and patient determine that the potential benefit of the medical therapy outweighs the risks and requirements for the medical therapy, the physician may obtain the required data or consent for prescribing the medical therapy. The data may include the patient's name, medical history, or insurance information, for example. Alternatively, this required data may already be present with the physician or has been obtained as part of the initial physician-patient consult. A particular medical therapy may require that certain diagnostic tests be performed prior to, during, or after medical therapy has concluded. For example, for a teratogenic drug, a negative pregnancy test may be required for a female capable of becoming pregnant to receive and continue to receive a teratogenic drug. Other medical therapies may require periodic tests or physician examinations to determine that the adverse effects associated with the medical therapy continue to be outweighed by the potential benefits for this patient. For example, baseline and periodic white blood cell counts must be taken to determine whether to continue dispensing Clozaril® (clozapine).

A patient or a physician may be required to provide informed consent for the medical therapy. A patient may need to acknowledge receipt of data about the medical therapy's adverse effects or potential for adverse effects, as well as the proper standard of care for administering the medical therapy. The patient or physician may need to agree to certain requirements associated with the restricted access, for example, a certification to follow all of the listed requirements for access to the medical therapy. As a condition for prescribing the medical therapy to a potential patient, a prescribing physician may determine that the patient is a qualified patient for a prescription as a function of the patient's fertility and informed consent and the physician's certification and initial risk level assessment.

In some aspects, after the patient is evaluated, characterized as to risk category and counseled, the attending physician may then obtain a written consent from the patient indicating that the patient has given truthful information and has been counseled by the physician. The informed consent may be very detailed in some aspects, in which the patient acknowledges that the patient understands the risks involved in taking the high risk medical therapy, agrees to follow the instructions and procedures instituted by the attending physician or distributor, including any necessary birth control measures or diagnostic tests to initiate and continue receiving the high risk medical therapy, agrees to take responsibility for informing their sexual partners of the risks and seek their cooperation in complying with the instructions provided or bring their partners to counseling as well if needed, and agrees to make any life-style changes necessary to benefit from using the high risk medical therapy. The patient may also agree to immediately inform the attending physician or the distributor in case the patient knows or suspects that the instructions were not understood or followed or that the patient is pregnant or was responsible for impregnating another. The patient may further agree to participate in patient surveys conducted by or on behalf of the distributor or the attending physician at random or regular intervals. The survey could be interactive, over the phone or in person or via on-line, for example. The survey information may become part of the patient history file and could be used by the attending physician and the distributor in their assessment either to initiate or to continue with the high risk drug medical therapy. The patient may also certify that any relevant information changes will be immediately reported to the attending physician or the distributor.

Based on available information, the physician may determine the risk level of the patient. For example, a patient could be characterized as "contraindicated", "high risk", "average risk". When an adverse event of the high risk medical therapy is of such severity that the risk of using the given medical therapy outweighs the benefits from using the medical therapy in a given patient, the medical therapy may be "contraindicated" to that patient or others similarly situated. Contraindications may arise, for example, due to a given patients' characteristics such as age, gender, race, physiologic conditions, e.g., failing kidney, compromised liver function, weakened heart, or concurrent therapy with another drug or medical therapy. Typically, the contraindications to a medical therapy generally would be specified in its approved labeling. The condition that causes a patient to become contraindicated to a high risk medical therapy may be temporary or permanent. For example, the use of a teratogenic drug generally would be contraindicated in pregnant patients because these drugs are known to pose an unacceptable risk to the fetus. Similarly, the use of a drug that causes irreversible toxicity to an organ may be contraindicated in those patients who have compromised organ function. A medical therapy could also be contraindicated for a particular patient based on the patient's responses to informed consent.

If the patient initially is characterized as contraindicated, a physician generally would not prescribe the medical therapy. Over time, however, a patient of average or high risk may become a contraindicated patient, based on a change in physical factors or response to the medical therapy or compliance with the risk management program or the medical therapy's labeling requirements. A contraindicated patient may in time be reclassified as an average risk or high risk patient, based on a change in circumstances or demonstrated ability to comply with the risk management program, or labeling requirements.

A "high risk patient" may be characterized as a patient who may be harmed by the high risk medical therapy without careful monitoring and delivery by a distributor of the medical therapy, as described herein, to prevent the treatment from becoming contraindicated at some future point. For example, with teratogenic drugs, a fertile female patient may be characterized as a high risk patient even if she is not pregnant at the start of the therapy. If the fertile female patient becomes pregnant during therapy with a teratogenic drug, she could then become contraindicated for the drug and may be required to immediately stop using the drug and return any unused medication to the drug distributor or physician for destruction. In this manner, a high risk patient may later be characterized as a contraindicated patient based on a change in patient-related or medical therapy-related conditions. Consequently, a high risk patient may need closer monitoring or restricted distribution by the physician and distributor than other patients, e.g., average risk patients, described below, to prevent the usage of the drug under instances for which it could be contraindicated.

An "average risk patient" may be characterized as someone for whom the drug is not contraindicated and ordinarily the patient will not be characterized as a high risk patient either. For example, with teratogenic drugs, a female patient who cannot become pregnant is an average risk patient. Since this patient is by definition not currently pregnant, she would not be generally a contraindicated patient absent risk characteristics, e.g., inability to follow instructions or product labeling requirements, and ordinarily would not be characterized as a high risk patient in the future. Average risk patients, however, may still experience some adverse events while taking the high risk drug, sometimes requiring discontinuation of the treatment.

A high risk patient may be characterized over time as an average risk patient that does not require close-monitoring or restricted distribution. For example, a fertile female patient at the start of the therapy with a teratogenic drug may become, during the treatment period, incapable of becoming pregnant due to advanced age or hysterectomy, requiring less close monitoring or restricted distribution to continue the therapy.

Because an average risk patient would not be characterized as a high risk or contraindicated patient, a patient may be preferably characterized as "average risk" only after the patient has been ruled out as a contraindicated or high risk patient.

Once it is determined that a patient may be treated with a medical therapy, the attending physician may counsel the patient concerning the risks involved, procedures to be followed, and behavior to be adhered to for the patient to remain eligible for further treatment. The attending physician may be required to counsel the average risk and high risk patients, prior to at least the initiation of the therapy. Average risk patients could be informed of their risk status and explained the various factors to watch for, which may change the patient's risk status to high risk or contraindicated. In some aspects, the average risk patient may need no more further counseling. However, both the patient and the attending physician may still engage in continuing counseling.

The counseling provided to a high risk patient by the attending physician or the distributor may include a full disclosure of the risk involved, the signs and symptoms of such risk the patient may be able to know or notice or watch for, preventive or protective steps the patient should take to avoid the risk, and activities the patient should undertake in case the patient has failed to understand or implement the physician's or distributor's instructions or counsel. For example, with teratogenic drugs, such counseling may include informing patients that such drugs must never be used by pregnant women and that even a single dose of the drug may cause birth defects and instructing patients to practice abstinence or to use two forms of birth control, e.g., for females, a hormonal form such as an oral, injectable, or implantable preparation with their male partner using physical barrier-type method, such as a condom. Counseling may include instructing a patient that if the patient fails to follow these instructions or suspects a pregnancy or, for male patients, suspects impregnating a female through unprotected sexual intercourse or otherwise, e.g., semen donation, the patient immediately should contact the attending physician or the distributor. As with all drugs, high risk patients may be counseled against sharing their medication with anyone else, particularly anyone who may also be a high risk patient. In some instances, patients may be made aware that they should not participate in blood donations until, for example, at least four to six weeks after the high risk medical therapy has been discontinued.

The attending physician or the distributor may provide high risk patients with a contraceptive or barrier method, e.g., a prescription for a hormonal therapy or a condom. In some instances, the attending physician may refer a high risk patient to a specialist such as an obstetrician-gynecologist for additional counseling on methods to avoid pregnancy or impregnation. The counseling may include warnings that no single birth control measure may be completely effective, and that a pregnancy may still occur, while on birth control.

For teratogenic drugs, a fertile female patient may be characterized as a high risk patient only after a negative serum test for pregnancy, prior to initiating the medical therapy and, for example, approximately every two to four weeks while on the medical therapy to confirm the negative result. In most instances, the drug may be provided for no more than approximately a two to four weeks supply. In general, follow-up visits to the attending physician may be necessary for most high risk patients to continue to receive the drug. During these visits, a patient could be re-evaluated based on the latest patient information, including the patient's current risk level. For example, a high risk patient may be re-characterized as an average risk patient or a contraindicated patient depending on any new information reviewed by the physician, or may remain a high risk patient.

High risk patients may be engaged in counseling throughout their therapy, unless their risk status changes during their course of treatment. Counseling may be provided at periodic intervals, for example, before the patient is provided the next course of medication. Counseling may also be provided on an as needed basis during the periodic intervals.

The physician may also provide the prescription for the medical therapy and required data for the qualified patient to a distributor. This prescription may be submitted to a distributor for further processing and subsequent filling and dispensing of the therapy to the patient. The distributor may be the manufacturer of the medical therapy, for example, or a wholesale distributor with or without a manufacturing facility. Alternatively, the physician may directly dispense or direct someone under supervision to dispense the therapy to the patient.

The distributor preferably has on staff several qualified physician experts who have been trained to identify and evaluate the risk factors inherently involved in treating patients with high risk medical therapies. The physicians on staff may be employees or consultants for the distributor to make an independent evaluation of the data supplied by the attending physician de novo. The staff physician may agree or disagree with the attending physician's evaluation or initial risk level characterization and may require additional information from the patient or attending physician. In any case, the staff physician generally will make the final decision if a consensus could not be reached and the patient may be denied the medical therapy drug at that point, but this decision may be reviewed and reversed in the future as new information becomes available.

In some aspects, the staff physician would not ordinarily interfere with or question the attending physician's practice relating to the initial diagnosis of the patient's symptoms, conclusion as to the patient's disease condition, and the need for this particular high risk medical therapy as a therapeutic choice. The staff physician's primary role would be to ensure that all the necessary risk-relevant information has been collected and carefully evaluated, the risks involved have been considered, the patient has been fully counseled and informed, and that the patient has promised to adhere to certain practices and behaviors such that she remains to be eligible for future treatment. The staff-physician, therefore, may become another layer of protection to ensure that the medical therapy is not contraindicated for this particular patient at this particular time and that risk-management system could be duly implemented. With a closer review by the distributor's staff physician, the distributor may provide another unhurried review of the patient's risk-related data that could be more than ministerial. Accordingly, the current practice of registering a pharmacy, physician, or patient involved in dispensing the high risk medical therapy may be excluded, without decreasing in the rigorousness of the review process and thereby achieving practical economies for the parties involved.

Once a patient's risk level characterization is complete, it generally would not be changed, unless there are compelling reasons. A change in the patient's age, health status, or results of a diagnostic test may alter the patient's assessed risk level. For certain high risk drugs, such as thalidomide, once a patient is characterized as an average risk patient, the patient may ordinarily remain as an average risk patient. This approach may cause less confusion in administering this program. This categorization method may be inherently better than previously known methods, because it could permit certain categories of patients to be defined, e.g., average risk patients, that require less intensive monitoring and may help conserve valuable physician resources. A majority of the patients treated with some high risk drugs, such as thalidomide, may be characterized as average risk patients, e.g., if a majority of patients are no longer fertile females or fertile males.

As additional risk-relevant information becomes available, a patient's risk level may be re-characterized. For example, if the medical therapy is a high risk teratogenic drug, such as thalidomide, a pregnant patient who is initially characterized as contraindicated may be re-characterized as a high risk patient and be eligible for access to the drug once the pregnancy is resolved and the attendant risk-related factors, e.g., lactating have disappeared. Similarly, a fertile female who is not pregnant before or during treatment with a teratogenic drug may be initially characterized as a high risk patient, but the patient may be re-characterized as average risk if additional information, such as the patient's inability to conceive in the future, becomes available. Additional information that may be obtained to facilitate a change in a patient's characterization may include results of a diagnostic test, results of additional counseling by the attending physician or the distributor or voluntary disclosure of additional information by the patient. This activity of shifting patients from one category to another could be entirely dependent on the nature of the medical therapy and the risk-relevant information associated with and the patient. For example, if the medical therapy is another teratogenic drug such as isotretinoin, it is possible that a majority of the patients may be categorized as high risk patients rather than average risk patients, given the customary patient population for isotretinoin consists of young adults. The present methods are designed to provide the high risk drug under these scenarios as well.

Alternatively, as additional information becomes available about the pharmacological, toxicological, teratogenic, tumorigenic or other clinical data of a medical therapy that was once-considered to be a high risk medical therapy, the medical therapy itself may be re-characterized as having a reduced risk, such as an average risk medical therapy. In such case, the distribution system contemplated may be adjusted to facilitate distribution of the medical therapy with limited or no special restrictions, other than the usual restrictions ordinarily placed on the medical therapy, or those that are unique to the medical therapy.

For example, as more information on teratogenicity of teratogenic drugs such as isotretinoin, thalidomide, lenalidomide, and related drugs are known, it is contemplated that the characterization of such drugs may be changed from being high risk to being average risk. Thus, in one aspect, the present invention provides a method for distributing a medical therapy previously characterized as high risk, wherein such method comprises distributing the medical therapy as an average risk medical therapy upon evaluation of relevant clinical, statistical, demographic and other evidence. It is appreciated that such evaluation may be made by, for example, the distributor, manufacturer, a body of physicians, or a regulatory body, such as the FDA. This change in categorization may also be made pertinent to one or more specific indications while the same medical therapy may retain its categorization for some other indication or treatment.

For example, thalidomide or lenalidomide or its analogues may remain as high risk drugs for certain indications or treatments, such as for treating anxiety, Hanson's disease, or some other ailment, while they may be considered as low risk for treating prostate cancer, or multiple myeloma, or myloplastic syndromes. Thus, the present invention contemplates a method of distributing a high risk medical therapy, wherein the medical therapy was previously characterized as high risk and is re-characterized as average risk or low risk. Such distribution may be made by the drug manufacturer or distributor. In a similar manner, a medical therapy that was once characterized as average risk may also be changed from average risk to high risk, for example, for specific patient populations or indications, requiring additional distribution controls.

In one embodiment, the present invention contemplates providing a medical therapy, wherein the medical therapy being distributed was previously characterized as a high risk therapy and required a specific distribution program. The specific distribution program may have required previously registering in a computer either a physician to prescribe the drug, the patient to receive the drug, the pharmacy or a wholesaler to distribute the drug, or a combination of these registrations before the patient received the medical therapy. Following the re-characterization of the medical therapy as having a reduced risk, the medical therapy may now be distributed without one or more of the registrations in a computer of the physician to prescribe, the patient to receive, or the pharmacist or wholesaler to distribute said drug. The educational materials or labeling of the medical therapy, accordingly, would typically be revised to reflect the one or more reduced drug distribution requirements.

For example, a medical therapy that comprises treatment with a drug such as thalidomide or lenalidomide may have been previously distributed pursuant to a registration program such as STEPS® or SEAT® or some other restricted distribution program for the medical therapy in accordance with an FDA policy or guidance. The restricted distribution program may have required registration in a computer database of a physician before the physician prescribes the drug to a patient, of a patient before the patient is eligible to receive the drug from a distribution party, e.g., pharmacy, wholesaler, or manufacturer, or of a distribution party before the drug may be distributed.

Following re-characterization of the medical therapy as having a reduced risk, the medical therapy is typically distributed according to this invention without requiring one or more of these registrations in a computer data base before the patient may receive the drug. As one example, thalidomide or lenalidomide could be distributed to the patient without the physician prescribing these drugs being previously registered in a computer database. Further, the drug may be distributed to the patient without the patient being previously registered in a computer database. Alternatively, the drug may be distributed to the patient without the distribution party being previously registered in a computer database.

The present invention comprises a method of collecting information for monitoring compliance on the usage of a medical therapy, pursuant to a health agency's directive or request on a specific treatment. For example, with thalidomide or lenalidomide, the restricted distribution program initially comprised collecting or analyzing at least patient and physician data from a computer readable database generated or maintained by a distribution party or manufacturer to confirm to the distribution party or regulatory body that the distribution program functioned as intended.

The patient information that may have been collected, compiled and or analyzed could include: patient age, gender, medical condition for which the drug may be prescribed, diagnosis details such as symptoms, diagnostic tests, previous treatments, any concurrent medications or therapies, drug allergies, other physiological incapacities such as liver disease, heart disease, kidney disease, or metabolic disorders, the duration and extent of previous and current therapies, outcomes or progression of the current therapy, or results of ongoing diagnostic tests, or final patient outcome, i.e., whether the patient was cured, under remission, or the therapy failed. The physician-specific information that may have been collected, compiled and or analyzed could include: the physician's name, address, affiliation, state and federal license numbers, medical specialty, years of practice, or any additional skills needed to understand the therapy being prescribed.

These data may be stored by the distribution party, the physician, or some other third party with database administration or management capabilities. Software programs and computer equipment as described herein may be used to set up the database and other administrative activities. Those programs may be used or can be readily tailored to meet the revised requirements of the restricted distribution program, distribution party, or regulatory body.

For example, hospitals and pharmacies typically use databases as part of their routine prescription-filling process. Following the re-characterization of the medical therapy as having a reduced risk, the software and computer equipment could be modified to utilize the data that is recorded in these alternative databases, such as the hospital or pharmacy databases, to record the data that continues to be required to be collected by the distribution party or regulatory body.

In another embodiment, where the medical therapy is re-characterized as having an increased risk, additional distribution controls may be added by the distribution party or required by a regulatory body for distribution. These additional controls may include additional data collection requirements by the distribution party, or one or more registrations of the patient, prescribing physician, or distribution party prior to the distribution party providing the medical therapy to the patient in need of the therapy. Additional controls may include required patient education materials, revised product labeling to reflect the additional information collected about the medical therapy or distribution requirements, or additional diagnostic testing prior to, during, or following treatment with the medical therapy.

Additional controls may be developed as consistent with the additional pharmacological, toxicological, teratogenic, tumorigenic, or other clinical data obtained from the medical therapy. A re-characterizing of the medical therapy may restrict the therapy to only certain patient populations or for the treatment of certain indications. In these situations, other medical therapies may prove to be safer or more effective for these patient populations or for the treatment of these indications. In these situations, these additional distribution controls may be added to the labeling for the medical therapy, or become part of a more restrictive risk management program, as described above.

The distributor may review the prescription and required data for the qualified patient and determine whether the patient met the requirements and is, therefore, eligible for access to the medical therapy. For example, this distributor could determine that the required data were complete and accurate, verifying certain information where appropriate. The distributor could also record data associated with the patient and physician in a computer readable medium, for record keeping purposes and to facilitate other data collection, following distribution of the medical therapy.

Following an initial review of the patient's data, this distributor could consult with the qualified patient or the qualified patient's physician. The consultation could be voice-recorded for record-keeping, and may help to determine whether the qualified patient should be provided access to the medical therapy. For example, this distributor could verify medical coverage, a physician's medical license or Drug Enforcement Administration (DEA) registration number that the physician has examined this patient, or a patient's understanding of the data associated with the medical therapy and its restricted access.

If the distributor determines that the patient is average risk, for example, the patient may be given the opportunity to obtain the high risk medical therapy at any pharmacy or retail distributor, similar to other prescription medical therapies but may involve additional record keeping requirements. Additional record-keeping requirements could be providing copies of the retail pharmacy distribution of the drug reported to a central distributor. The patient's physician or a distributor of the medical therapy could provide the medical therapy to a patient characterized as average risk or high risk. High risk patients, however, normally would be monitored and counseled closely before, during, and after treatment. Patients characterized as contraindicated would be denied access to the medical therapy, unless they were later reclassified as average risk or high risk patients.

If the distributor determines that the patient should be characterized as high risk, it could deliver, as appropriate, the medical therapy to the patient or designated delivery agent for the patient. The distributor may designate a pharmacy, manufacturer, or distributor to deliver the medical therapy. The distributor may use, for example, a conventional, confirmed delivery mechanism that obtains a signature upon delivery. Alternatively, a patient's eligibility may be determined by a third party that is neither a distributor nor a manufacturer, or even a pharmacy. When this third party determines that the patient is eligible for access to the medical therapy, it could deliver, as appropriate, the medical therapy to the patient or designated delivery agent for the patient. The third party may designate a pharmacy, manufacturer, or distributor to deliver the medical therapy.

Alternatively, if it is not possible for the high risk, eligible patient to sign for the delivery, the distributor could send the medical therapy, for example, to the patient's physician or pharmacist, provided the medical therapy is delivered according to applicable laws or labeling requirements for the medical therapy.

Alternatively, the confirmed delivery of the medical therapy to the eligible patient may be recorded in a database available in a computer readable medium, along with other prescription relevant data. For example, the distributor could record data in a central database including the patient's name, prescription delivered, a copy of the prescription labeling for this patient, and data concerning the distribution party's determination that the patient should be provided access to the medial therapy in this instance and the patient's assigned risk level, which may include a voice recording of the distribution authority confirming the informed consent from the qualifying patient.

The distributor may also put in additional record keeping or recording methods to keep the activity under close surveillance. For example, the distributor's interactions with the attending physician, the patients, and any pharmacists involved, as well as any mandatory counseling or follow-up surveys may be recorded on an audio-recordable medium, which can be further transcribed and stored in a computer readable/recordable and retrievable medium, following dispensing of the medical therapy. This safeguards all the parties involved with reliable records, and, if a mistake happens in the process, it may be noticed and corrected.

Alternatively, or in addition, a confirmation letter or a copy of the prescription or other prescription relevant data may be provided to the eligible patient's physician to aid in determining the patient's potential for future medical therapy.

Following a distribution of the medical therapy, the distributor may obtain additional data from the eligible patient or the eligible patient's physician to assess the patient's eligibility to obtain the medical therapy in a subsequent prescription, for quality control, or as required by a regulatory authority, e.g., FDA, that monitors the distribution of the restricted access medical therapy.

This invention may be implemented using one or more processing devices. The processing devices may be coupled such that portions of the processing or data manipulation may be performed at one or more processing devices and shared or transmitted between a plurality of processing devices.

As an example of the invention, the following network environment is described in detail. Specifically, FIG. 1 shows a network environment 100 adapted to support the present invention. The exemplary environment 100 includes a network 104, a server 102, a plurality of communication appliances, or user locations, or subscriber devices, or client terminals, 110(a) ... (n) (where "n" is any suitable number) (collectively referred to herein as, client terminals 110) and the remote client terminals, represented by terminal 120.

The network 104 is, for example, any combination of linked computers, or processing devices, adapted to transfer and process data. The network 104 may be private Internet Protocol (IP) networks, as well as public IP networks, such as the Internet that can utilize World Wide Web (www) browsing functionality.

Server 102 is operatively connected to network 104, via bi-directional communication channel, or interconnector, 112, which may be for example a serial bus such as IEEE 1394, or other wire or wireless transmission medium. The terms "operatively connected" and "operatively coupled", as used herein, mean that the elements so connected or coupled are adapted to transmit and/or receive data, or otherwise communicate. The transmission, reception, or communication is between the particular elements, and may or may not include other intermediary elements. This connection or coupling may or may not involve additional transmission media, or components, and may be within a single module or device or between the remote modules or devices.

The server 102 is adapted to transmit data to, and receive data from, client terminals 110 and 120, via the network 104. Server 102 is described in more detail with reference to FIG. 2, herein.

Client terminals 110 and 120 are typically computers, or other processing devices such as a desktop computer, laptop computer, personal digital assistant (PDA), wireless handheld device, and the like. They may be capable of processing and storing data themselves or merely capable of accessing processed and stored data from another location, i.e., both thin and fat terminals. These client terminals 110, 120 are operatively connected to network 104, via bi-directional communication channels 116, 122, respectively, which may be for example a serial bus such as IEEE 1394, or other wire or wireless transmission medium. Client terminals 110, 120 are described in more detail in relation to FIG. 3.

The server 102 and client terminals 110, 120 typically utilize a network service provider, such as an Internet Service Provider (ISP) or Application Service Provider (ASP) (ISP and ASP are not shown) to access resources of the network 104.

Figure 2:
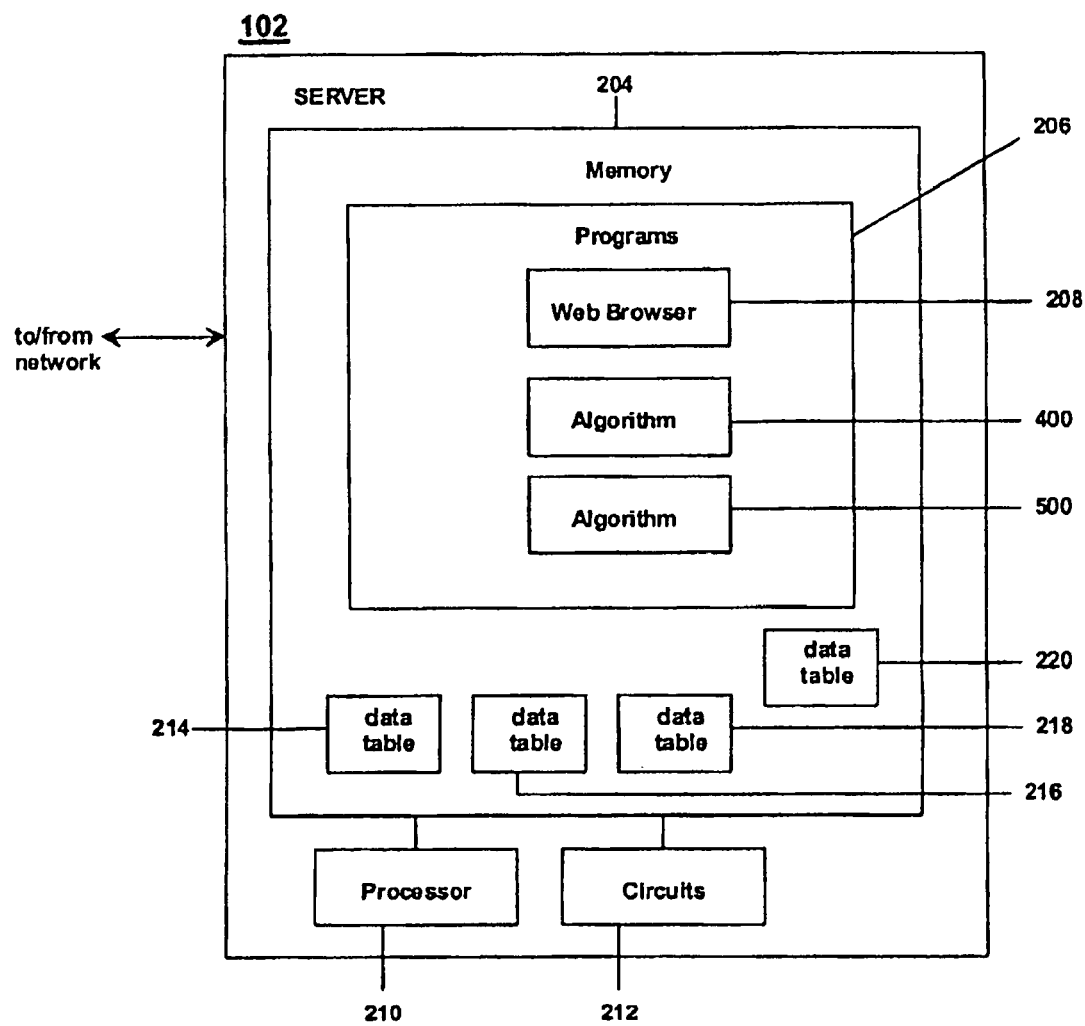
FIG. 2 illustrates a processing apparatus adapted to store and process data related to the present invention.

FIG. 2 illustrates that server 102, which is adapted to store and process data related to the present invention, is operatively connected to the network (shown as 104 in FIG. 1), via interconnector 112. Server 102 includes a memory 204, processor 210 and circuits 212.

Memory 204 stores programs 206, which include, for example, a web browser 208, algorithm 400, as well as typical operating system programs (not shown), input/output programs (not shown), and other programs that facilitate operation of server 102. Web browser 208 is for example an Internet browser program such as Internet Explorer®. Algorithm 400 is a series of steps for manipulating selected data, which is typically stored on a computer-readable memory and executed by a processor. The process of the present invention typically generates a record of a delivered medical therapy to a patient in accordance with a physician's prescription and requirements for restricted access. These functions may be implemented or facilitated by using software or other program code to sort the data and generate the representation. The algorithm 400 is discussed in more detail in relation to FIG. 4.

Memory 204 also stores data tables 214, 216, 218, and 220. These data tables are databases or memory locations adapted to store related data, which can be retrieved, processed, updated, modified or otherwise manipulated.

For example, data table 214 may be adapted to store prescription data related to a first patient; data table 216 may be adapted to store prescription data related to a second patient; and data table 218 may be adapted to store prescription data related to a third patient. Data table 220 may be adapted to store a subset of data collected from each patient. A patient's prescription data could include, for example, the patient's social security number, address, prescribing physician, and diagnostic test results. This data is typically obtained in relation to the physician's determination that a particular medical therapy would be indicated or could be beneficial for a patient.

Processor 210, which is operatively connected to memory 204, is used to process and manipulate the data retrieved and stored by server 102 or from another device coupled to system 100. The processor 210 is typically a microprocessor with sufficient speed and processing capacity to adequately perform the desired data manipulations, of server 102. Circuits 212 are operatively connected to processor 210 and typically include, for example, Integrated Circuits (ICs), ASICs (application specific ICs) power supplies, clock circuits, cache memory and the like, as well as other circuit components that assist in executing the software routines stored in the memory 204 and that facilitate the operation of processor 210.

Figure 3:
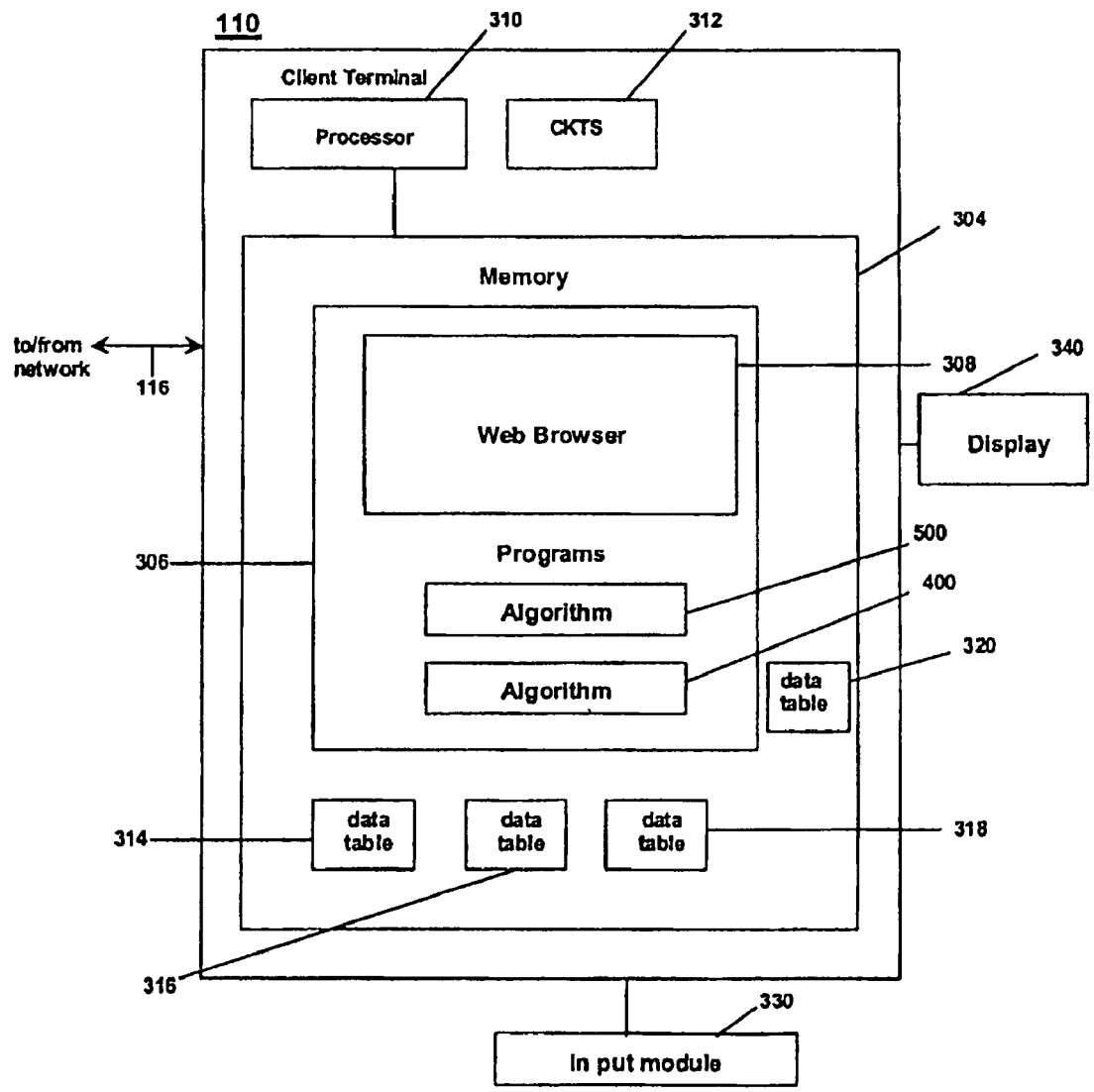
FIG. 3 illustrates a communication appliance shown in FIG. 1.

FIG. 3 illustrates subscriber terminal, also referred to herein as a client terminal, user terminal, or communication appliance 110. Terminal 110 is typically a desktop computer, laptop computer, PDA (personal digital assistant), wireless handheld device, mobile phone, or other device capable of interfacing with a network, such as an IP network. Terminal 110 includes processor 310, support circuitry 312, memory 304, input module 330, and display module 340. Bi-directional interconnection medium 116 operatively connects the terminal 110 to the network (shown as element 104 in FIG. 1). The user terminal is typically located at the user location.

Processor 310, which is operatively connected to memory 304, is used to process and manipulate the data retrieved and stored by terminal 110. The processor 310 is typically a microprocessor with sufficient speed and processing capacity. The processor 310 is operatively connected to circuitry 312. Circuitry 312 typically includes, for example, Integrated Circuits (ICs), ASICs (application specific ICs) power supplies, clock circuits, cache memory and the like, as well as other circuit components that assist in executing the software routines stored in the memory 304 and that facilitate the operation of processor 310.

Memory 304 stores programs 306, which include, for example, a web browser 308, algorithm 400, as well as typical operating system programs (not shown), input/output programs (not shown), and other programs that facilitate operation of terminal 110. Web browser 308 is for example an Internet browser program such as Internet Explorer®. Algorithm 400 is a series of steps, typically executed by a processor such as, for example, processor 310, to manipulate selected data from the client terminal. Algorithm 400 is discussed in more detail in relation to FIG. 4.

Memory 304 also stores data tables 314, 316, 318, and 320. These data tables are databases or memory locations adapted to store related data, which can be retrieved, processed, updated, modified, or otherwise manipulated.

Data table 314 is adapted to store prescription data related to a first patient; data table 316 adapted to store prescription data related to a second patient; and data table 318 is adapted to store prescription data related to a third patient. Data table 320 is adapted to store a subset of the data collected for each patient. A patient's prescription data could include, for example, the patient's social security number, address, age, gender, allergies, current medications the patient is taking, any affecting disorders or ailments such as diabetes or hypertension, prescribing physician, and diagnostic test results. This data is typically obtained in relation to the physician's determination that a particular medical therapy would be indicated or could be beneficial for a patient.

Input module 330 is, for example, a keyboard, mouse, track ball, touch pad, menu having soft-keys, or any combination of such elements, or other input facility adapted to provide input to terminal 110.

Display module 340 is, for example, a monitor, LCD (liquid crystal display) display, GUI (graphical user interface) or other interface facility that is adapted to provide or display information to a user. Other display modules could include a printer or other output module.

Figure 4:
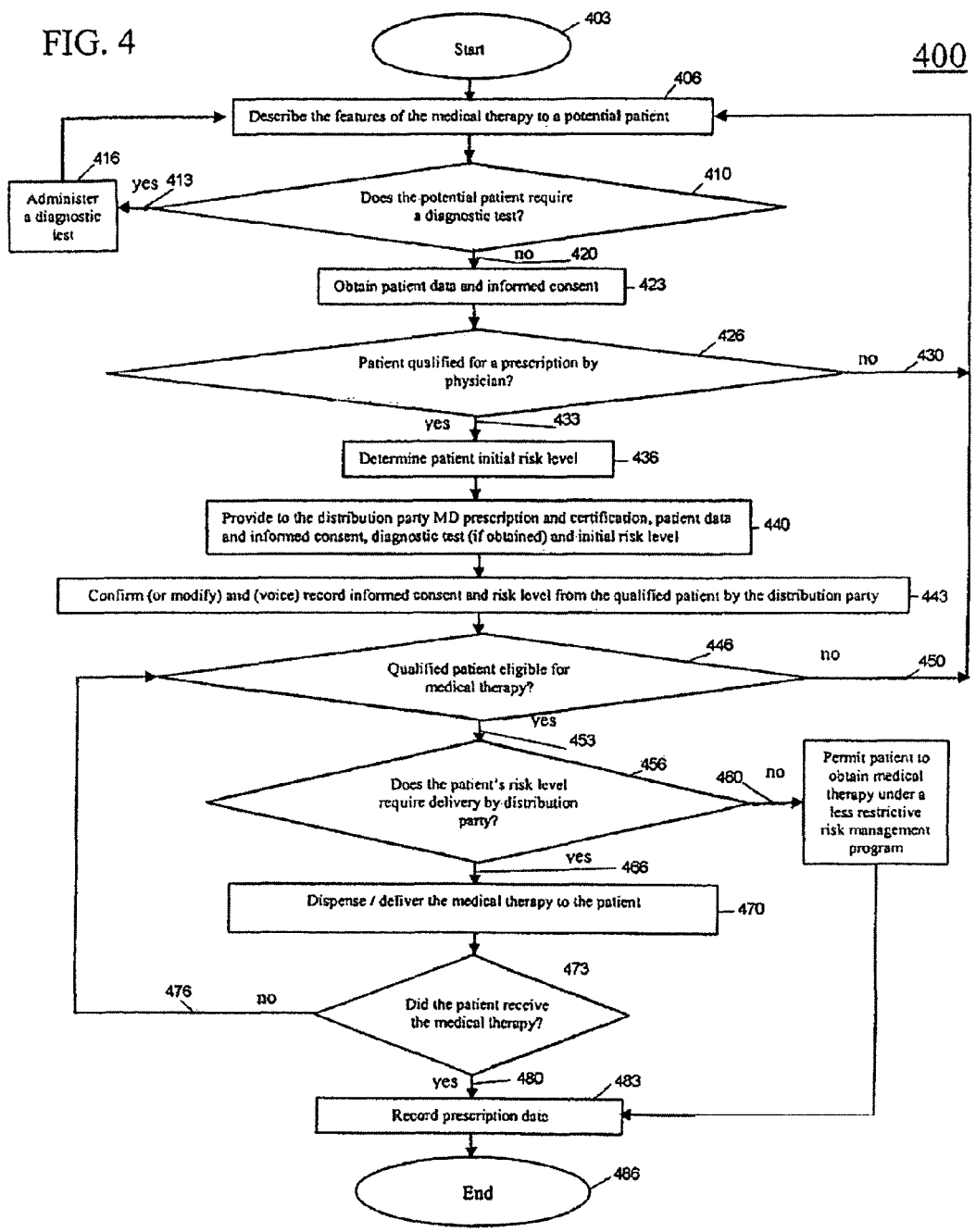
FIG. 4 is a flowchart of one embodiment of the present invention.

Generally, the present invention is achieved in several steps, the order of which may vary for a particular patient or medical therapy. A general discussion of several embodiments of the invention are discussed below, with more specific embodiments discussed in relation to FIG. 4. For example, FIG. 4 illustrates how a patient's risk level may be used to determine whether a medical therapy may be delivered under a less restrictive risk management program. FIG. 4 also illustrates how a medical therapy may be distributed following the administration of one or more diagnostic tests and patient informed consent. This illustration, therefore, describes only one of a variety of distribution methods or systems possible with the present invention.

As shown in FIG. 4, algorithm 400 is a series of steps, some or all of the steps may be stored on a computer-readable medium that may be executed at a server, client terminal, or other processing device to implement the present invention. Step 403 begins execution of the algorithm. Step 406 shows the requirement to describe the features of a medical therapy to a patient to obtain access to the medical therapy. Typically the features of the medical therapy would be identified by a patient's physician, primarily based on the approved labeling for the medical therapy. These features could include, for example, data regarding the risks and benefits associated with the medical therapy and the restricted distribution system. These features may also include the specific requirements for obtaining a prescription from the patient's physician, as well as the additional requirements for eligibility that are reviewed and assessed by the distributor. One of additional requirements could include, for example, diagnostic tests administered on a patient. In the case of the teratogenic drug thalidomide, diagnostic tests may include a pregnancy test, if the patient is a fertile female.

Step 410 determines whether the patient requires a diagnostic test for the patient's physician to determine whether the medical therapy would be prescribed for this patient. In the case of thalidomide, for example, if the patient is a fertile female, the patient would need to obtain a pregnancy test, to determine that the patient is not pregnant prior to initiating therapy, and at regular intervals during therapy once initiated, because thalidomide is a teratogenic drug and may not be prescribed or distributed to pregnant females. Other drugs, such as Clozaril® (clozapine) require other periodic diagnostic tests, e.g., white blood count to obtain continued prescriptions, because it is not possible to assess which patients will be contraindicated for the drug therapy until actually beginning the therapy. If the answer to step 410 is "yes", line 413 leads to step 416. If the answer to step 410 is "no", line 420 leads to step 423.

Step 416 administers a diagnostic test to a patient. As described in step 410, the nature of the diagnostic test will be determined by the patient's physician, as determined by the requirements identified in the approved labeling for the medical therapy and other relevant information. In many cases, the patient will need to consent to this procedure, as determined by the patient's physician, which is separate and distinct from the consent described below for access to the medical therapy itself.

Step 423 obtains the required patient data and informed consent for prescribing the medical therapy. The required data could include the patient's social security number, home address, and other identifying information, medical history, or other information as required, such as the diagnostic test administered in step 416 in some instances. The patient's informed consent typically includes representations by the patient that the patient will follow the requirements for access to the medical therapy. For instance, with thalidomide, a patient could agree to use one or more forms of birth control to prevent a pregnancy while taking the drug.

Typically, once this information is received, it will be reviewed by the patient's physician to determine whether a prescription for the medical therapy appears to be appropriate for this patient, as indicated in the determining step 426. If the physician determines that the patient should be prescribed this medical therapy under its conditions, typically, as in the case with thalidomide, the physician must also certify that the patient is qualified for a prescription and that the physician will monitor and follow the requirements associated with the restricted distribution of the medical therapy. In some instances, the physician's prescription alone may be sufficient to satisfy this certification requirement, depending on the specific medical therapy involved. If the physician decides to prescribe the medical therapy, line 433 leads to step 436.

If the physician determines that the patient should not be prescribed the medical therapy, line 430 leads to step 406, where the physician would describe the features of the medical therapy that indicate why the patient would not qualify to obtain a prescription at this time for the medical therapy. In the example risk categories provided, this patient would be classified as contraindicated. In some instances, a patient could qualify for a prescription at a future date, for example, in the case of thalidomide, if a diagnostic test indicated that a patient were a pregnant female, the patient's physician could prescribe thalidomide in the future after the patient were no longer pregnant. As another example, a patient that provided a deficient informed consent, e.g., the patient did not agree to follow one or more of the requirements of the restricted distribution program, could in the future become qualified by a physician, if the physician determined that the patient understood and would follow the one or more requirements that were previously determined by the physician to be deficient and otherwise qualifying for a prescription of the medical therapy.

For all patients who are not contraindicated for the medical therapy, the patient's physician would determine in step 436 an initial risk level based on the labeling and known risks for the medical therapy and any information collected from the patient e.g., diagnostic tests or responses provided during the informed consent process. In the example provided, for a teratogenic drug such as thalidomide, fertile females and fertile males would be characterized as "high risk" (or contraindicated), based on the potential risk to a fetus for exposure to the drug by the patient's use of the drug. Non-fertile females and non-fertile males, on the other hand, could be classified as "average risk", requiring less oversight and monitoring, which may involve additional options for obtaining the drug, e.g., directly from a retail pharmacy.

Step 440 provides to the distributor certain preliminary information for the distributor to consider whether the now qualified patient with a prescription would be eligible for receiving the medical therapy. In many instances, this information could be provided by the patient's physician. The data may be received from a user terminal, web page, network device or other source of image data or sample data, and is typically transmitted over a network or other transmission medium. For example, data would be typically obtained via facsimile from a doctor's office and sent to the distributor. The data would include the physician's prescription and certification (where applicable) and the patient's data, including any required diagnostic tests, informed consent, and initial risk level assessment by the patient's physician. Some of this data may differ, depending on the particular patient. For example with thalidomide, data associated with a fertile female patient would include a negative pregnancy test (negative, because if it were positive, the patient's physician would not have found the patient qualifying for a prescription), whereas data associated with a fertile male patient would not include a negative pregnancy test. In the example risk levels, a fertile female and fertile male would be characterized as "high risk" (or contraindicated). In addition, most non-fertile female and non-fertile males would be classified as "average risk" (or contraindicated) based on other factors e.g., inclination to share the drug with fertile female or fertile males or inclination to follow the conditions for obtaining or using the high risk drug.

In step 443, the distributor confirms the informed consent provided by the patient and may voice-record this conversation. Depending on the requirements of the restricted distribution program, this step may also involve describing the features of the medical therapy or restricted access program to the qualified patient. For example with thalidomide, this confirmation step could include verifying that the qualified patient has been provided with and understands all of the necessary information to provide informed consent, i.e., risks and benefits of thalidomide, including its teratogenic effects, viewing or reading any instructional materials such as videotapes or product labeling brochures, and the requirements applicable to this qualified patient for becoming eligible to receive thalidomide from the distributor. In other instances, the distributor may gather additional information in the process of confirming the qualified patient's informed consent, which can then be used for the distributor to determine eligibility for delivery of the medical therapy to this qualified patient and the patient's risk level. For example, the distributor may gather additional information concerning the qualified patient's concomitant medication use or medical history, or willingness to comply with the requirements for delivery of the restricted access medical therapy.

Step 446 determines whether the qualified patient is eligible for delivery of the restricted access medical therapy. At this stage of the process, in those cases where the medical therapy is not directly dispensed or provided by the physician, the documents provided in step 440 will be reviewed by the distributor. Further, the distributor has confirmed or listened to the voice-recording of the qualified patient's informed consent in step 443. The distributor may require additional information at this stage if, for example, the qualified patient's informed consent indicates that additional information should be obtained from the qualified patient's physician. As a matter of standard operating procedures (SOPs), the distributor may also routinely obtain certain information, such as calling the qualified patient's medical insurance provider to verify treatment for certain disease conditions or medical coverage for the medical therapy.

After the distributor makes its decision, if the answer to step 446 is "no", line 450 leads to step 406. If the answer to step 446 is "yes", line 453 leads to step 456. Similar to the process in step 406 following line 430, in step 406 following line 450, if the distributor determines that the qualified patient is ineligible for delivery of the medical therapy, the distributor will then describe the features of the medical therapy and indicate why the qualified patient would not be eligible to obtain a prescription at the present time. In some instances, a qualified patient could become eligible for delivery by the distributor at a future date. For example, in the case of thalidomide, if the distributor were unable to reach the qualified patient within a certain time period, certain diagnostic tests related to requirements could become outdated. In the case of thalidomide, a diagnostic test for a qualified female patient could be a negative pregnancy test. If the negative pregnancy test were conducted outside the prescribed time period, as indicated in the restricted distribution program, the qualified patient could become eligible for delivery by submitting a complying pregnancy test to the distribution party. As another example, a patient that provided a valid written informed consent but then was unable to confirm the informed consent during the initial discussion with the distributor in step 443 may subsequently confirm the informed consent after the qualified patient's physician has had a chance to describe the features of the medical therapy to the patient once more in step 406.

Step 456 determines whether the risk level assigned by the distribution party requires the distribution party to be responsible for delivering the medical therapy to the qualified patient. This step provides a process to differentiate how the high risk drug is provided to patients with different risk levels as assessed by the physician and distributor.

When a high risk medical therapy is first marketed to patients, a regulatory agency such as the FDA may require that it be distributed to all patients in a particular risk management program. Over time, as more information is collected regarding the prescribing patterns for the medical therapy and adverse events observed, it may become possible for certain patients to be excluded from the original risk management program or placed on a less restrictive risk management program or RiskMAP. For example, with the teratogenic drug thalidomide, if a female is no longer menstruating, it may be appropriate to assess this patient's risk at a lower level e.g., average risk rather than high risk, because there is no risk that the female patient could expose a new or developing fetus to the drug by the female's use of the drug. In this circumstance, it would be beneficial to provide the drug to the patient in a less restrictive manner than for other patients who could expose a fetus to the drug.

If the answer to step 456 for a patient with a lower assessed risk level may be "no", line 460 leads to step 463 which permits the lower risk patient to obtain the medical therapy under a less restrictive risk management program. One type of less restrictive manner would be to permit this patient to obtain the medical therapy directly from the pharmacy without requiring a distributor to confirm informed consent and the risk level assessment with each prescription or refill. Similarly, a higher risk patient could in time be reassessed as a lower risk, or average risk patient, because, e.g., the formerly fertile patient is no longer menstruating. Whether a patient is initially or later assessed as a lower risk patient, the patient could obtain the medical therapy under a less restrictive risk management program. This type of program would lead to greater efficiencies in compliance and monitoring the risk management program for the high risk medical therapy, because resources could be directed to the higher risk patients. In situations where the lower risk patient could once again become a higher risk patient, e.g., the non-fertile female becomes fertile again by the use of hormones or another medical therapy or physical operation, the lower risk management program or RiskMAP could include a mechanism for periodic reassessment of patient eligibility for the lower level risk program and reassignment to a higher level risk management program. As with other prescription drugs, once this lower risk patient obtained the medical therapy, step 483 records the prescription data for this patient, as described more fully below.

If the answer to step 456 is "yes", line 466 leads to step 470 to dispense or deliver the medical therapy to the patient. For example, the delivery may be by next day delivery with a return receipt and delivery only upon signature by the patient. In most instances, the medical therapy will be delivered with a means for verifying the delivery.

Step 473 determines whether the patient has received the medical therapy. Receipt may be verified by a return receipt with a signature. Alternative means may be used to confirm receipt, for example, receipt by a receiving authority for the patient, including, but not limited to, the patient's physician or pharmacist. If the answer is "no", line 476 leads to step 446, where the distributor adds this information along with the previously received information and determines whether the patient still meets the requirements for access to the medical therapy. At the distributor's discretion, in some situations, for example, the patient may be contacted to determine the reason for non-receipt and re-authorize the delivery of the medical treatment. In other situations, additional diagnostic tests may be required (re-tests). In still other situations, the patient's physician or both the patient and patient's physician may be contacted for additional information for the distributor to consider in its determination.

If the answer step 473 is "yes", the delivery of the medical therapy to the patient will be recorded when step 480 is reached. In step 483 the data recorded may include, for example, a copy of the patient's prescribing label, the patient's data and diagnostic tests and voice-recorded confirmation of informed consent provided in step 443, and the reasons for determining that the qualifying patient was eligible for delivery of the medical therapy, including the patient's risk level, as assessed by the distribution party. If certain additional data is obtained verbally as part of a consultation, these discussions also may be voice-recorded and made part of this record. These records may be printed, displayed, transmitted to a location, such as a user terminal, other location designated by a user, or a memory coupled to the server, or processing device, executing certain aspects of algorithm 400. For example, the prescription data recorded in step 483 may be supplemented with additional prescribing data for this or other medical therapies by the distributor. In addition, the prescription data may be accessed by the distributor, manufacturer of the medical therapy, or other regulatory body for quality control of the delivery process or for obtaining statistical or other data, as described in other embodiments of the present invention.

The algorithm ends, as shown in step 486.

The following example is a summary of a restricted drug access program that could utilize the present invention for generic thalidomide. In this example, the manufacturer of the thalidomide product is also the distributor.

Example

Safe and Efficient Access to Thalidomide (SEAT™)

Proposed Standard Operating Procedures (SOPs)

1. Physician/Patient Counseling
   a. The potential patient's physician reads the thalidomide labeling and all SEAT™ program information with updates as appropriate prior to counseling the patient.
   b. The physician explains to the patient thalidomide, its risks and benefits, SEAT™, and all the elements to receive and continue to receive thalidomide under SEAT™.
   c. The physician determines if the patient is a female of capable of becoming pregnant, and, if so, explains the additional program requirements for her, and administers the diagnostic pregnancy test, if the patient agrees to proceed. Additional diagnostic tests may be administered as determined by the physician.
   d. The physician obtains patient data and informed consent from the patient.
   e. Upon determining that the patient is qualified for a prescription, the physician determines the patient's initial risk level and writes a prescription for thalidomide for the patient (now a qualified patient) and certifies the physician's conclusions that the patient is qualified and agrees to follow the requirements of SEAT™.

2. Physician Sends Via Facsimile the Qualified Patient's Informed Consent, Physician's Prescription and Certification, Patient's Initial Risk Level, and Qualified Patient's Negative Pregnancy Test (for Fertile Females).
   a. Information from the Physician
      i. The manufacturer ensures that the form is correctly and completely filled out, including all necessary signatures or initials. The manufacturer will initial to indicate that the form has been reviewed (date/time) and whether there are additional items that require clarification from the physician or qualified patient.
      ii. The manufacturer verifies the patient's home address with the patient's date of birth and social security number.
      iii. The manufacturer verifies the patient's insurance information and coverage.
      iv. The manufacturer researches the physician and patient from its prescription database and other records, including physician license or DEA registrations. If the patient was a former or current thalidomide patient, the manufacturer verifies the last time that thalidomide was dispensed. Where possible, the manufacturer verifies signatures or other identifying information.

v. If the patient is a female and the physician did not send a negative pregnancy test, the manufacturer verifies that the physician indicated that the patient is not capable of becoming pregnant.

vi. If the patient has obtained thalidomide through their insurance company, the manufacturer determines that the patient has not received duplicate prescriptions and that there have been no irregularities with the prescriptions.

vii. The manufacturer verifies that the physician has seen this patient for quality control and clarifies any items that have not been answered fully in the form.

b. Information from a Retail Pharmacist i. The pharmacist informs a qualified patient that there is a generic product available and will have the patient fill out a form, including a request for thalidomide from the manufacturer's SEAT™ program and agreement to follow terms of SEAT™, consent to release medical records, and phone number with date/time for the manufacturer to call and confirm informed consent from the qualifying patient. The pharmacist forwards this information to the manufacturer and the qualifying patient's physician via facsimile, along with the patient's insurance information, and shipping and billing instructions for the pharmacy. The instruction for the patient's physician includes a physician certification/prescription form, a phone number to send via facsimile this form along with the patient's informed consent, negative pregnancy test, and other relevant patient information, such as the physician's determination of the patient's initial risk level. The manufacturer requests that the physician sends this information on the same day that it is received from the pharmacist.

ii. The manufacturer ensures that the form is correctly and completely filled out, including all necessary signatures or initials. The manufacturer initials to indicate that the form has been reviewed (date/time) and whether there are additional items that require clarification from the physician or patient.

iii. The manufacturer verifies the patient's home address with the patient's date of birth and social security number.

iv. The manufacturer verifies the patient's insurance information and coverage.

v. The manufacturer researches the physician and patient from its database and other records, including physician license or DEA registration. If the patient was a former or current thalidomide patient, the manufacturer will verify the last time that thalidomide was dispensed. Where possible, the manufacturer verifies signatures or other identifying information.

vi. If the patient is a female and the physician did not send a negative pregnancy test, the manufacturer verifies that the physician indicated that the patient is not capable of becoming pregnant.

vii. If the patient has obtained thalidomide through their insurance company, the manufacturer determines that the patient has not received duplicate prescriptions and that there have been no irregularities with the prescriptions.

viii. The manufacturer verifies that the physician has seen this patient for quality control and clarifies any items that have not been answered fully in the form. The manufacturer verifies that the physician has seen this patient and determines whether the physician is willing to prescribe generic thalidomide for this patient. If not already provided, the manufacturer asks the physician to send a copy of the negative pregnancy test (if required), the patient's informed consent, the patient's initial risk level, and a SEAT™ physician certification/prescription form to the manufacturer. The manufacturer sends the physician a copy of the necessary SEAT™ documents for future prescriptions.

3. Qualified Patient and Manufacturer Confirmation of Informed Consent (Voice-Recorded)

a. The manufacturer calls the qualified patient at the phone number and during the date/time indicated on the information submitted.

b. The manufacturer informs the qualified patient that the call will be recorded for their safety and quality control and then verifies the patient's information, e.g., patient name, Social Security number, address, date of birth, and shipping information.

c. The manufacturer asks the patient questions designed to confirm that the patient has provided informed consent.

d. The manufacturer asks questions to verify that the patient understands SEAT™ by asking the patient to explain the program to the manufacturer, the risks and benefits associated with thalidomide, including its teratogenic effects, and why the patient believes the patient's physician has prescribed thalidomide for the patient.

e. The manufacturer assesses from its confirmation of informed consent and the information submitted for the patient whether the patient is willing to comply with SEAT™, especially concerning pregnancy testing, birth control measures, and reporting adverse events and pregnancies that occur while on thalidomide. The manufacturer ensures that the patient understands that if the patient becomes pregnant, the patient must immediately stop using thalidomide and must obtain additional pregnancy counseling from the manufacturer and their prescribing physician.

f. The manufacturer's pharmacist reviews the information forms and initial consult and then screens the patient for potential drug-drug and drug-disease interactions or other concerns for this patient.

g. If the manufacturer decides that the patient is not eligible for delivering thalidomide at this time, e.g., a contraindicated patient, the manufacturer provides additional counseling or delays the prescription to a later date and notifies the physician of its decision.

h. If the manufacturer decides based on this information that this patient is eligible for delivery of thalidomide, the manufacturer determines the eligible patient's risk level, e.g., high risk or average risk. If the patient's risk level does not require delivery by the manufacturer, e.g., average risk, the manufacturer permits the patient to obtain the medical therapy under a less restrictive risk management program. This less restrictive management program will still involve prescription data to be recorded to permit for cross validation that the patient has not inappropriately received thalidomide. In addition, the less restrictive management program provides a mechanism to periodically reassess the risk level of the patient, in case circumstances change and the patient should be assessed at a higher or lower risk level, or becomes contraindicated for the drug.

i. For patients whose risk level requires delivery by the distribution party, e.g., high risk patients, the manufacturer verifies the patient's insurance information and verifies other information as appropriate. The patient has now been confirmed to be eligible to receive the medication from the manufacturer.

j. The manufacturer ships the prescription to the eligible patient via next day delivery with signature confirmation (only by addressee). If it is not possible for the patient to sign, the manufacturer may also send the prescription to a pharmacist or physician, as long as they dispense it (date recorded) prior to seven days from the last pregnancy test, if applicable. If the patient's pharmacist has forwarded the prescription, the manufacturer ships the prescription to the pharmacist, so the pharmacist may dispense the drug to the patient with the pharmacist's label.

k. Once the manufacturer confirms a signed receipt of the thalidomide by the eligible patient or the patient's designated physician or pharmacist, the manufacturer records the prescription in its prescription database and sends a letter to the eligible patient's physician that that prescription was filled, including a copy of the prescription label.

l. The manufacturer will update its prescription database for each eligible patient, as appropriate, based on new information provided to the manufacturer, including additional voice-recorded discussions with the manufacturer's dedicated support system and its risk level assessment.

4. Manufacturer Follow-Up Survey a. The manufacturer will ask follow up questions to eligible patients as necessary for quality control and to determine how the patient's therapy is proceeding.

b. The manufacturer will take the appropriate steps to intervene with additional counseling or to delay a subsequent prescription as necessary based on a patient's response to any of the preceding questions. The manufacturer's healthcare provider (pharmacist, physician, or registered nurse) will be available to offer additional counseling and help, to receive a report of any adverse events, or to help investigate the suspicion of a pregnancy associated with thalidomide use. These subsequent discussions will be voice-recorded and added to the prescription database.

5. Subsequent prescriptions a. The process begins as previously described with the physician to patient counseling, modified as appropriate, with a repeat pregnancy test (if needed).

The invention may further involve a method for delivering a high risk medical therapy comprising:

receiving prescription data and certification data from a qualified patient's physician, including diagnostic data and informed consent from the qualified patient, and a risk level of the patient as determined by the qualified patient's physician, wherein the qualified patient's physician or designated assistant has previously:

provided information related to the medical therapy to a patient;

determined whether the patient requires a diagnostic test to qualify for the medical therapy;

administered any required diagnostic tests to the patient;

obtained informed consent from the patient, wherein the consent includes representations by the patient that the patient will follow requirements for access to the medical therapy;

determined that the patient is a qualified patient for a prescription as a function of patient data and the informed consent from the patient;

determined the risk level of the patient as a function of the patient data and the informed consent;

included in the certification data conclusions from the qualified patient's physician that the patient is a qualified patient for a prescription of the medical therapy and representations that the qualified patient's physician will follow the requirements for access to the medical therapy;

confirming the informed consent from the qualified patient by the distributor;

determining that the qualified patient is eligible for access to the medical therapy;

determining the risk level of the patient by the distributor;

permitting the patient to obtain the medical therapy in a less restrictive risk management program, based upon the risk level of the patient as determined by the distributor;

recording prescription data including the risk level of the patient and eligibility information.

The method above, further comprising:

providing the prescription data to the eligible patient's physician.

The method above, further comprising:

obtaining additional data from the qualified or eligible patient to determine present or future qualification or eligibility for the medical therapy, including patient risk level, or for quality control.

The method above, wherein the eligible patient is a male capable of impregnating a female.

The method above, further comprising recharacterizing the medical therapy to a lower risk category; and adjusting the distribution system to a less restrictive risk management program.

The method above, further comprising distributing the medical therapy with fewer restrictions.

The method above, further comprising distributing the medical therapy independent of registering a physician.

The method above, further comprising distributing the medical therapy independent of registering a patient.

The method above, further comprising distributing the medical therapy independent of registering the distribution party.

The method above, further comprising modifying a data collection method for obtaining patient, physician, or distribution party data under the less restrictive risk management program.

The method above, further comprising labeling the medical therapy to reflect the less restrictive risk management program.

The method above, wherein the medical therapy initially was provided with limited or no special restrictions, other than the usual restrictions ordinarily placed on the medical therapy, and the medical therapy is re-characterized to a higher risk category requiring additional distribution controls, including the controls described above.

The method above, further comprising distributing the medical therapy with additional restrictions.

The method above, further comprising requiring additional data collection prior to distribution of the medical therapy.

The method above, further comprising requiring one or more registrations of the patient, prescribing physician, or distribution party prior to the distribution party providing the medical therapy.

The method above, further comprising distributing educational materials to the patient, prescribing physician, or distribution party.

The method above, further comprising revising the product labeling to reflect additional information collected about the medical therapy or distribution requirements.

The method above, further comprising requiring additional diagnostic testing prior to, during, or following treatment with the medical therapy.

The method above, further comprising limiting the distribution of the medical therapy to certain patient populations.

The method above, further comprising limiting the distribution of the medical therapy for the treatment of certain indications.

The method above, wherein the medical therapy is from the group consisting of thalidomide, lenalidomide, isotretinoin, bosentan, alosetron, dofetilide, oxycodone, marijuana, cannabis, and clozapine.

The method above, wherein the medical therapy is a product with the potential for substance abuse, or chemical dependency.

The method above, wherein the medical therapy requires ongoing diagnostic testing for continued therapy.

The invention may further involve a method for delivering a medical therapy to an eligible patient and preventing access to the medical therapy for patients for whom the drug is contraindicated comprising:

receiving prescription data and certification data from a qualified patient's physician, including diagnostic data and informed consent from the qualified patient, and a risk level of the patient as determined by the qualified patient's physician, wherein the qualified patient's physician or designated assistant has previously:

identified one or more conditions to obtain access to a medical therapy;

provided data to a patient related to the medical therapy and related requirements;

obtained required data for prescribing the medical therapy;

qualified the patient for a prescription of the medical therapy by the patient's physician as a function of the patient's required data for prescribing the medical therapy and an informed consent from the patient;

determined the risk level of the patient as a function of patient data and the informed consent from the patient;

included in the certification data conclusions from the qualified patient's physician that the patient is a qualified patient for a prescription of the medical therapy and representations that the qualified patient's physician will follow the requirements for access to the medical therapy;

confirming the informed consent from the qualified patient by a third party reviewer, determining the qualified patient is eligible to receive the medical therapy;

determining the risk level of the patient by the third party reviewer; and permitting the patient to obtain the medical therapy in a less restrictive risk management program, based upon the risk level of the patient as determined by the third party reviewer.

The method above, further comprising:

recording prescription data, including the risk level of the patient, and eligibility information.

The method above, further comprising:

providing the prescription data to the eligible patient's physician.

The method above, further comprising:

obtaining additional data from the qualified or eligible patient to determine present or future qualification or eligibility for the medical therapy, including patient risk level, or for quality control.

The method above, further comprising re-characterizing the medical therapy to a lower risk category; and adjusting the distribution system to a less restrictive risk management program.

The method above, further comprising distributing the medical therapy with fewer restrictions.

The method above, further comprising distributing the medical therapy independent of registering a physician.

The method above, further comprising distributing the medical therapy independent of registering a patient.

The method above, further comprising distributing the medical therapy independent of registering a distribution party.

The method above, further comprising modifying a data collection method for obtaining patient, physician, or distributor data under the less restrictive risk management program.

The method above, further comprising labeling the medical therapy to reflect the less restrictive risk management program.

The method above, further comprising re-characterizing the medical therapy to a higher risk category that requires additional distribution controls.

The method above, further comprising distributing the medical therapy with additional restrictions.

The method above, further comprising requiring additional data collection prior to distributing the medical therapy.

The method above, further requiring one or more registrations of the patient, prescribing physician, or distribution party prior to the distribution party providing the medical therapy.

The method above, further comprising distributing educational materials to the patient, prescribing physician, or distribution party.

The method above, further comprising revising the product labeling to reflect additional information collected about the medical therapy or distribution requirements.

The method above, further comprising requiring additional diagnostic testing prior to, during, or following treatment with the medical therapy.

The method above, further comprising limiting the distribution of the medical therapy to certain patient populations.

The method above, further comprising limiting the distribution of the medical therapy for the treatment of certain indications.

The method above, wherein the medical therapy is re-characterized to a lower risk category and the distribution system is adjusted to facilitate distribution of the medical therapy with limited or no special restrictions, such as those described in claim 1, other than the usual restrictions ordinarily placed on the medial therapy, or those that are unique to the medical therapy.

The method above, wherein the medical therapy initially was provided with limited or no special restrictions, other than the usual restrictions ordinarily placed on the medical therapy, and the medical therapy is re-characterized to a higher risk category, requiring additional distribution controls, including the controls described in claim 1.

The method above, wherein the medical therapy is from the group consisting of thalidomide, lenalidomide, isotretinoin, bosentan, alosetron, dofetilide, oxycodone, marijuana, cannabis, and clozapine.

The method above, wherein the medical therapy is a product with the potential for substance abuse or chemical dependency.

The method above, wherein the medical therapy requires ongoing diagnostic testing for continued therapy.

The invention may further involve a method for delivering a high risk medical therapy comprising:
re-characterizing the medical therapy to a lower risk category; and
adjusting the distributing system to a less restrictive risk management program.

The method above, further comprising distributing the medical therapy with fewer restrictions.

The method above, further comprising distributing the medical therapy independent of registering a physician.

The method above, further comprising distributing the medical therapy independent of registering a patient.

The method above, further comprising distributing the medical therapy independent of registering a distribution party.

The method above, further comprising modifying a data collection method for obtaining patient, physician, or distributor data under the less restrictive risk management program.

The method above, further comprising labeling the medical therapy to reflect the less restrictive risk management program.

The method above, wherein the medical therapy is from the group consisting of thalidomide, lenalidomide, isotretinoin, bosentan, alosetron, dofetilide, oxycodone, marijuana, cannabis, and clozapine.

The method above, wherein the medical therapy is a product with the potential for substance abuse or chemical dependency.

The invention may further involve a method for delivering a medical therapy comprising:
re-characterizing the medical therapy to a higher risk category; and
adjusting the distribution system to a more restrictive risk management program.

The method above, further comprising distributing the medical therapy with additional restrictions.

The method above, further comprising requiring additional data collection prior to distributing the medical therapy.

The method above, further requiring one or more registrations of the patient, prescribing physician, or distribution party prior to the distribution party providing the medical therapy.

The method above, further comprising distributing educational materials to the patient, prescribing physician, or distribution party.

The method above, further comprising revising the product labeling to reflect additional information collected about the medical therapy or distribution requirements.

The method above, further comprising requiring additional diagnostic testing prior to, during, or following treatment with the medical therapy.

The method above, further comprising limiting the distribution of the medical therapy to certain patient populations.

The method above, further comprising limiting the distribution of the medical therapy for the treatment of certain indications.

The method above, wherein the medical therapy is from the group consisting of thalidomide, lenalidomide, isotretinoin, bosentan, alosetron, dofetilide, oxycodone, marijuana, cannabis, and clozapine.

The method above, wherein the medical therapy is a product with the potential for substance abuse or chemical dependency.

Thus, while fundamental novel features of the invention shown and described and pointed out, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in another form or embodiment. It is the intention, therefore, to be limited only as indicated by the scope of the claims appended hereto.

What is claimed is:

1. A method for delivering a medical therapy by a distributor comprising the distributor:
    a) receiving prescription data from a physician authorizing distribution of the medical therapy to a specific patient in need of the medical therapy,
    wherein the medical therapy was characterized as a high-risk medical therapy and the Food and Drug Administration (FDA) required a restricted distribution program, the elements of which distribution program comprised registering in a computer-readable storage medium prior to the distribution of the medical therapy to the patient all of the physician, the patient, and the distributor, and generating a validation code to dispense the medical therapy;
    b) confirming that the patient is eligible to receive the medical therapy;
    c) confirming that the patient understands risks associated with the medical therapy;
    d) distributing the medical therapy to the patient independent of requiring:
        (i) registration of either the physician, or the patient, or the distributor or a combination thereof, in a computer readable storage medium prior to distribution of the medical therapy; or
        (ii) a validation code to dispense the medical therapy;
    wherein,
    the risk level of the patient or medical therapy was recharacterized and FDA permitted the change to the restricted distribution program.

2. The method of claim 1, wherein the distributor is a pharmacy.

3. The method of claim 1, wherein the distributor is a wholesaler.

4. The method of claim 1, wherein the distributor is a party other than a pharmacy, a wholesaler or a physician.

5. The method of claim 1, wherein the validation code to dispense the medical therapy is provided by the manufacturer of the drug that is comprising the medical therapy, or a physician, or an entity that has contractual obligation with: a) the manufacturer of the drug; b) the distributor or wholesaler of the drug; or c) the owner of the drug approval package which has been authorized by a governmental health agency to market the drug.

6. The method of claim 1, further comprising providing a data collection method for obtaining patient, physician, or distributor data.

7. The method of claim 1, wherein the medical therapy comprises: a) a pharmaceutical dosage form comprising a drug substance for administration to the patient; and b) labeling to be accompanied with the dosage form.

8. The method of claim 1, wherein the medical therapy comprises the drug thalidomide.

9. The method of claim 1, wherein the medical therapy comprises the drug lenalidomide.

10. The method of claim 1, wherein the medical therapy comprises the drug isotretinoin.

11. The method of claim 1, wherein the medical therapy comprises a drug selected from the group consisting of: bosentan, alosetron, dofetilide, oxycodone, cannabis, and clozapine.

12. The method of claim 1, wherein the medical therapy is a product with the potential for substance abuse or chemical dependency.

13. The method of claim 1, further comprising limiting the distribution of the medical therapy to certain patient populations.

14. The method of claim 13, wherein the medical therapy comprises the drug thalidomide.

15. The method of claim 13, wherein the medical therapy comprises the drug lenalidomide.

16. The method of claim 13, wherein the medical therapy comprises the drug isotretinoin.

17. The method of claim 13, wherein the medical therapy comprises a drug selected from the group consisting of: bosentan, alosetron, dofetilide, oxycodone, cannabis, and clozapine.

18. The method of claim 13, wherein the medical therapy is a product with the potential for substance abuse or chemical dependency.

19. The method of claim 1, further comprising limiting the distribution of the medical therapy for the treatment of certain indications.

20. The method of claim 19, wherein the medical therapy comprises the drug thalidomide.

21. The method of claim 19, wherein the medical therapy comprises the drug lenalidomide.

22. The method of claim 19, wherein the medical therapy comprises the drug isotretinoin.

23. The method of claim 19, wherein the medical therapy comprises a drug selected from the group consisting of bosentan, alosetron, dofetilide, oxycodone, cannabis, and clozapine.

24. The method of claim 19, wherein the medical therapy is a product with the potential for substance abuse or chemical dependency.

* * * * *

UNITED STATES PATENT AND TRADEMARK OFFICE
CERTIFICATE OF CORRECTION

PATENT NO.       : 7,885,824 B1
APPLICATION NO.  : 11/478240
DATED            : February 8, 2011
INVENTOR(S)      : Phanesh Koneru It is certified that error appears in the above-identified patent and that said Letters Patent is hereby corrected as shown below:

IN THE CLAIMS:

Col. 28, lines 37-38, Claim 1, under (c), should read as follows:

--conforming that the patient understands risks associated with the medical therapy; and--.

Signed and Sealed this
Nineteenth Day of April, 2011

David J. Kappos
*Director of the United States Patent and Trademark Office*